United States Patent
Edgington et al.

(10) Patent No.: US 9,995,663 B2
(45) Date of Patent: Jun. 12, 2018

(54) SAMPLE PREPARATION METHOD FOR ANALYSIS OF ACRYLAMIDE

(71) Applicant: Biotage AB, Uppsala (SE)

(72) Inventors: Alan Edgington, Hengoed (GB); Lee Williams, Cardiff (GB)

(73) Assignee: Biotage AB, Uppsala (SE)

( * ) Notice: Subject to any disclaimer, the term of this patent is extended or adjusted under 35 U.S.C. 154(b) by 51 days.

(21) Appl. No.: 14/914,995

(22) PCT Filed: Aug. 29, 2014

(86) PCT No.: PCT/EP2014/068444
§ 371 (c)(1),
(2) Date: Feb. 26, 2016

(87) PCT Pub. No.: WO2015/028643
PCT Pub. Date: Mar. 5, 2015

(65) Prior Publication Data
US 2016/0209304 A1 Jul. 21, 2016

(30) Foreign Application Priority Data
Aug. 30, 2013 (EP) .................................. 13182372

(51) Int. Cl.
*G01N 1/40* (2006.01)
*B01D 11/02* (2006.01)
(Continued)

(52) U.S. Cl.
CPC ............. *G01N 1/405* (2013.01); *B01D 11/02* (2013.01); *G01N 1/4055* (2013.01); *G01N 33/02* (2013.01);
(Continued)

(58) Field of Classification Search
CPC ...... G01N 1/405; G01N 33/025; G01N 33/10; G01N 33/14
See application file for complete search history.

(56) References Cited

U.S. PATENT DOCUMENTS 3,008,990 A * 11/1961 Weiss .................... C07C 233/09
564/129
4,810,822 A * 3/1989 Sidot .................... C07C 233/45
562/567

(Continued)

FOREIGN PATENT DOCUMENTS

GB 2472404 A 2/2011

OTHER PUBLICATIONS

Agilent Technologies, Inc., Analysis of acrylamide in chocolate, chips, waffles, coffee and cacao powder, Oct. 31, 2011.*

(Continued)

*Primary Examiner* — David Bolduc
(74) *Attorney, Agent, or Firm* — Harness, Dickey & Pierce, P.L.C.

(57) ABSTRACT

The present invention relates to a method for extracting acrylamide from a matrix comprising matrix components and acrylamide, comprising the steps: bringing said matrix in contact with water to obtain an aqueous extract, and, optionally, adding a base to the aqueous extract; loading a portion of the aqueous extract obtained in the previous step onto an inert support; allowing the inert support to absorb the aqueous extract; extracting acrylamide from the aqueous extract by passing a water immiscible organic solvent through the inert support; thereby obtaining an organic extract. It further relates to a method for analyzing acrylamide content in a matrix comprising matrix components and acrylamide.

8 Claims, 4 Drawing Sheets

(51) Int. Cl.
*G01N 33/02* (2006.01)
*G01N 33/10* (2006.01)
*G01N 33/14* (2006.01)
*G01N 30/06* (2006.01)

(52) U.S. Cl.
CPC ........... *G01N 33/025* (2013.01); *G01N 33/10* (2013.01); *G01N 33/14* (2013.01); *G01N 2001/4061* (2013.01); *G01N 2030/062* (2013.01)

(56) References Cited

U.S. PATENT DOCUMENTS

| | | | | |
|---|---|---|---|---|
| 6,160,086 | A * | 12/2000 | Holm | C08F 6/003 264/211.14 |
| 7,122,640 | B2 * | 10/2006 | Gjerde | B82Y 30/00 210/656 |
| 7,193,065 | B2 * | 3/2007 | Sigler | C07K 16/44 435/7.5 |
| 2004/0058046 | A1 * | 3/2004 | Zyzak | A21D 8/042 426/549 |
| 2004/0081724 | A1 * | 4/2004 | Dria | A23F 5/163 426/52 |
| 2004/0101607 | A1 * | 5/2004 | Zyzak | C12Y 305/01001 426/425 |
| 2004/0265429 | A1 * | 12/2004 | Teras | C12Y 305/01001 426/52 |
| 2006/0210669 | A1 * | 9/2006 | Howie | A23G 1/02 426/45 |
| 2008/0009488 | A1 * | 1/2008 | Anand | C07D 409/14 514/230.5 |
| 2012/0181232 | A1 | 7/2012 | Chen | |
| 2013/0017545 | A1 * | 1/2013 | Yong | G01N 1/405 435/6.12 |
| 2013/0233093 | A1 * | 9/2013 | Pohl | G01N 1/10 73/863.21 |
| 2013/0324523 | A1 * | 12/2013 | Kudo | A61K 9/0019 514/230.5 |
| 2014/0033805 | A1 * | 2/2014 | Nema | G01N 1/28 73/61.55 |
| 2014/0263050 | A1 * | 9/2014 | Sowa, Jr. | B01D 11/0492 210/633 |
| 2015/0010676 | A1 * | 1/2015 | Ozeki | C12N 9/80 426/60 |
| 2016/0109417 | A1 * | 4/2016 | Nunoshige | B01J 20/288 422/70 |

OTHER PUBLICATIONS

Achim Claus et al, "A method for the determination of acrylamide in bakery products using ion trap LC-ESI-MS/MS", Molecuklar Nutrician & Food Research, vol. 49, No. 10, Oct. 2005, pp. 918-925.

Thierry Delatour et al, "Improved Sample Preparation to Determine Acrylamide in Difficult Matrixes Such as Chocoalte Powder, Cocoa, and Coffee by Liquid Chromatography Tandem Mass Spectroscopy", Journal of Agricultural and Food Industry, vol. 52, No. 15, Jul. 2004, pp. 4625-4631.

Eden Tareke et al, Analysis of Acrylamide, a Carcinogen Formed in HEated Foodstuffs, Journal of Agricultural and Food Chemestry, vol. 50, No. 17, Aug. 2002, pp. 4998-5006.

Bellah O Pule et al, "Determination of Acrylamide in Cooking Oil by Agilent Bond Elut Quechers Acrylamide Kit and HPLC-DAD Authors" Jan. 6, 2012.

V. Yusa et al, "Determination of Acrylammide in foods by pressurized fluid extraction and kliquid chromatography-tandem mass spectrometry used for a survey of Spnish cereal-based foods", Food Additives and Contaminants, vol. 23, No. 3, Mar. 2006, pp. 237-244.

V Gokmen et al, "Multiple-stage extraction strategy for the determination of acrylamide in food", Journal of Food Composition and Analysis, Academic Press, London, GB, vol. 22, No. 2, Mar. 2009, pp. 142-147.

International Search Report PCT/ISA/210 for International Application No. PCT/EP2014/068444 dated Feb. 2, 2015.

* cited by examiner

SAMPLE PREPARATION METHOD FOR ANALYSIS OF ACRYLAMIDE

FIELD OF THE INVENTION

The present invention relates to preparation of samples for analysis of acrylamide. In particular, it relates to preparation of food samples by Supported Liquid Extraction (SLE).

BACKGROUND OF THE INVENTION

Acrylamide analysis has become an area for expansion in recent years with the linking of the carcinogenic molecule with a number of fried or roasted foods and drinks. Tareke et al. (Tareke, et al., 2002) highlighted the potentially carcinogenic properties of the analyte combined with the levels present in foods that have been fried or baked. Analysis in industry is particularly common for coffee and fried potato chips (crisps).

Acrylamide is a very small and polar compound. Because of its polar nature it is extremely difficult to measure using techniques employed by laboratories which are normally designed for the analysis of larger more non polar compounds. Due to its high polarity and the difficult nature of the matrices many sensitive methods for acrylamide analysis in the literature involve two separate extraction procedures (one performed directly after the other) with methods being expensive, complicated and time consuming to perform. The majority of literature methods require two solid phase extractions (e.g. (Roach, et al., 2003)), one after the other, making analysis both time consuming and expensive. Other methods in the literature include relatively complicated two stage procedure for the extraction, cleanup and enrichment of acrylamide (Claus, 2005), a liquid-liquid extraction (Delatour, et al., 2004), that is time consuming and difficult to automate, and a less sensitive QuEChERS method (Pule & Torto, 2012).

Supported liquid extraction (SLE) uses the same extraction principles as traditional liquid-liquid extraction (LLE), which is based on analytes partitioning from an aqueous based matrix into a water immiscible organic solvent. The traditional LLE approach is more suited to less polar analytes that are more likely to partition out of the water based matrix into the water immiscible extraction solvent. Polar analytes are more water soluble, preferring to remain in the water phase and are more difficult to extract into the water immiscible organic solvent using LLE or SLE. Polar analytes are therefore usually extracted using a Solid Phase Extraction (SPE) approach.

According to standard method development strategies (Biotage, 2013) for Isolute® SLE+, a good choice of extraction solvent for extracting a neutral analyte is a water immiscible organic solvent in which the analyte is freely soluble, such as MTBE, dichloromethane and ethyl acetate for a polar compound. If the compound does not elute well in those solvents, it is proposed to add up to 5% of a polar modifier such as isopropanol. It is warned that the use of higher amounts of polar (water miscible) modifiers in the extraction solvent can lead to co-extraction of some matrix components.

SUMMARY OF THE INVENTION

The present invention relates to extraction of acrylamide from a matrix, such as a food matrix, by means of Supported Liquid Extraction using a water immiscible organic solvent for extraction of acrylamide from the matrix.

DEFINITIONS

ISOLUTE, TurboVap, and SPE Dry are trademarks of Biotage AB, Uppsala, Sweden.

That a solvent is "water immiscible" shall be construed to mean that it has a solubility in water of less than 10% at 25° C.

That a solvent is "water miscible" shall be construed to mean that it has a solubility in water of essentially 100% at 25° C.

DETAILED DESCRIPTION OF PREFERRED EMBODIMENTS OF THE INVENTION

The present inventors have realized that there is a need for a rapid, straightforward and sensitive analysis of acrylamide from matrices, such as food matrices. The inventors have surprisingly found that this can be achieved by Supported Liquid Extraction using a water immiscible solvent, or a mixture of organic solvents, as extraction solvents.

In a first aspect, the invention relates to a method for extracting acrylamide from a matrix comprising matrix components and acrylamide, comprising the steps
 a) bringing said matrix in contact with water to obtain an aqueous extract, and, optionally, adding a base to the aqueous extract;
 b) loading a portion of the aqueous extract onto an inert support;
 c) allowing the inert support to absorb the aqueous extract;
 d) extracting acrylamide from the aqueous extract by passing a water immiscible organic solvent through the inert support;
thereby obtaining an organic extract.

In a preferred embodiment of the invention, the aqueous extract loaded onto the inert support in step b) is the, optionally basified, aqueous extract obtained directly from step a).

The matrix may be any matrix that contains or is suspected of containing acrylamide. This may be matrices in environmental samples, such as earth, soil, or wastewater, textiles, paper, cosmetics, tissues and body fluids from animals and humans, or food samples.

Potentially acrylamide containing food matrices that may be prepared by the method according to the invention include essentially all processed food wherein the food processing method may induce acrylamide formation. Without being bound by theory, it has been hypothesized that acrylamide is formed at elevated temperatures in cooking, especially in carbohydrate-rich foods (Tareke, et al., 2002). It has also been hypothesized that acrylamide results from heating of equimolar amounts of glucose and some amino acids, primarily asparagine and methionine, but also alanine, arginine, aspartic acid, cysteine, glutamine, threonine and valine (Friedman, 2003). Examples of such potentially acrylamide containing food matrices include potato (including crisps, or chips, French-fried, deep-fried, and boiled potato), coffee, almonds, asparagus, baked products (including bread, cakes, cookies, pretzels, biscuits, crackers, crispbread), malt based drinks (including beer), cereals, chocolate powder, corn chips, fish, meat, poultry, nuts, peanuts, nut and peanut butter, vegetable based snacks, soybeans, sunflower seeds, taco shells (Friedman, 2003).

The method comprises a first extraction of the acrylamide from the solids of the matrix into water. The particular way of doing this will depend on the characteristics of the matrix. A matrix comprising large pieces of matrix, such as potato crisps, cereals, meat or baked products, may be finely divided or crushed, mixed with water, and centrifuged to remove the solid matrix constituents. A powdered matrix, such as ground coffee or chocolate powder, may be prepared according to the same procedure as used for consumption.

An internal standard, i.e. a defined amount of acrylamide, may be added to the matrix before or during the first extraction. The acrylamide used as internal standard may be labelled, such as isotope labelled with $^{13}C$ or $^3H$, as known in the art.

For some heavily pigmented matrices, such as coffee, it may be desirable to add a base to the aqueous extract, such as ammonia solution. Although the sample added to the SLE column is darker as a result of the basification the final extract appears visibly cleaner than with untreated coffee.

The aqueous extract so obtained is then loaded onto a bed of an inert support material, preferably without further pre-treatment. The material is preferably diatomaceous earth, but any other inert support material, such as silica or silica-based materials, may be used as long as they are capable of retaining dispersed droplets of an aqueous sample on their surfaces. The material may be in a range of physical forms, such as a granulate or powder, preferably contained in a column or flow-through well of a plate, wherein the column or well has an inlet at the top and an outlet at the bottom, and the material is preferably contained in the column or well by liquid-permeable top and bottom frits. In some embodiments the inert support material may be in the form of a membrane. The aqueous extract is allowed to flow into the inert support material. It may be desirable to apply a positive pressure from the top or vacuum from the bottom to force the extract into the inert support.

As the aqueous extract flows into the particulate material, it spreads over the surface of the material, forming an immobilized layer of small droplets.

The extraction of acrylamide from the aqueous phase is performed by passing a water immiscible organic solvent through the inert support. When the water immiscible extraction solvent is applied for this elution step, it flows over the aqueous droplets allowing efficient acrylamide partitioning. The large surface area of the extraction interface and flow through nature of the technique leads to a very efficient extraction procedure, because acrylamide comes into contact with fresh solvent as the organic phase travels through the bed, mimicking a repeat LLE mechanism.

The water immiscible solvent may be any water immiscible solvent, or mixture of solvents, of sufficient polarity to allow extraction of acrylamide from the aqueous phase to the organic phase. Examples of water immiscible solvents that may be used are (polarity index within parentheses): ethyl acetate (4.4), methyl-tertiary butyl ether (2.5), dichloromethane (3.1), chloroform 4.1), butanol (4), butyl acetate (3.9), dichloroethane (3.5), dichloromethane (3.1), diethyl ether (2.8), benzene (2.7), xylene (2.5), toluene (2.4).

The water immiscible solvent may also be a mixture of a water immiscible solvent and a polar water miscible solvent. Such mixture of solvents should itself be water immiscible when used in accordance with the present invention. The addition of a polar water miscible solvent will enhance the extraction of acrylamide from the aqueous phase.

Examples of water immiscible solvents that are useful when mixed with water miscible solvents include, in addition to the water immiscible solvents listed above, hexane and heptane.

Examples of water miscible solvents that are useful in mixture with water immiscible solvents include tetrahydrofuran, n-propanol, iso-propanol, dioxane, acetone, methanol, ethanol, acetonitrile, acetic acid, dimethylformamide, dimethyl sulfoxide.

When using a mixture of water immiscible and water miscible solvents in accordance with the invention, the ratio between water immiscible and water miscible solvent may vary depending on the solvents comprised in the mixture, as long as the mixture as a whole retains its water immiscibility. At present, ratios of water immiscible to water miscible solvents in the range of 20:1 to 1:2 are contemplated, such as 10:1, 5:1, 4:1, 3:1, 2:1, 1:1, and 1:2.

The water immiscible solvent is allowed to flow under gravity through the bed of particulate material, whereby an organic extract is obtained. This organic extract is preferably collected in a separate collection container. Optionally, vacuum or positive pressure is applied to elute the solvent.

The collection container may further contain a further solvent with high boiling point (>100° C.), such as ethylene glycol, in order to prevent loss of analyte during the evaporation and reconstitution step.

In a further aspect, the present invention relates to a method for analysing acrylamide content in a matrix comprising matrix components and acrylamide, comprising the steps extracting acrylamide from the matrix according to the method according to the above aspect;

analysing acrylamide content of the so obtained organic extract.

The analysis may be performed as known in the art, LC-MS/MS or GC-MS

In a further aspect, the invention relates to a method for analysing acrylamide content in a matrix comprising matrix components and acrylamide, comprising the steps extracting acrylamide from the matrix according to the method according to the first aspect above;

removing the water immiscible organic solvent mixture from the obtained organic extract and reconstituting the extract in water;

analysing acrylamide content of the reconstituted extract by LC-MS/MS.

The invention will now be further illustrated by reference to examples. The examples are purely illustrative and not intended to limit the invention, which is as defined in the appended claims.

Example 1: Extraction of Acrylamide from Fried Potato Chips (Crisps) Using ISOLUTE SLE+ Prior to LC-MS/MS Analysis This example describes a Supported Liquid Extraction (SLE) protocol for the extraction of Acrylamide from potato chips/crisps using ISOLUTE SLE+ plates with LC-MS/MS detection.

This method achieves high recoveries of acrylamide in fried potato chips (crisps). The method is potentially sensitive enough to measure levels as low as 10 ppb if necessary in a range of potato chips including a selection of flavored and hand fried varieties.

Sample Preparation Procedure
Column Configuration:
ISOLUTE® SLE+ 1000 supported liquid extraction plate, (Biotage, Uppsala Sweden, part number 820-0140-C)
Sample Pre-Treatment:
25 g of crisps were finely crushed to a consistent sample using a pestle and mortar before being transferred to an airtight container. When required, between 0.99 and 1.01 g of crushed crisps was accurately weighed into a 15 mL screw capped centrifuge tube. This was spiked with 10 μL of internal standard solution. The crisps were then left for approximately 30 minutes to allow the solvents to evaporate and the acrylamide and internal standard to soak into the crisps.

Water (10 mL) was added to each tube.

The tubes were rotated for at least one hour at a relatively slow speed e.g. 20 rpm before centrifugation at 2875 g for 12 minutes. A 0.65 mL aliquot of the aqueous layer was removed taking care not to take up any of the thin upper oil layer Supported Liquid Extraction
Sample Loading:
Load pre-treated sample (0.65 mL) onto each well. Apply a pulse of vacuum (VacMaster-10 or 20 Sample Processing Manifold, 121-1016 or 121-2016) or positive pressure (Pressure+ Positive Pressure Manifold, PPM-48) to initiate flow. Allow the sample to absorb for 5 minutes.

Analyte Elution:
Elute with Ethyl acetate: Tetrahydrofuran, (1:1, v/v, 2×2.5 mL) and allow to flow under gravity into a tube containing 2 μL ethylene glycol in each well. Apply vacuum or positive pressure to elute any remaining extraction solvent.

Post Elution:
Dry the volatile constituents of the eluate in a stream of air or nitrogen using a SPE Dry (40° C., 20 to 40 L min$^{-1}$) or TurboVap 96 (15 bar at 40° C. for 1 hr). Reconstitute in water (200 μL)

HPLC Conditions
Instrument: Waters Acquity
Column: Phenomenex Hydro 4 μm 50×2 mm C18 column with a C18 guard cartridge and on-line filter
Mobile Phase: A: 0.1% formic acid in water B: 0.1% formic acid in methanol
Flow rate: 0.3 mL min$^{-1}$
Injection: 10 μL
Gradient: Initial 100% A, hold till 0.6 min
linear ramp to 100% B over 0.25 min (0.85 min), hold 1.65 min (2.5 min)
linear ramp to 100% A in 0.01 min, hold 2.49 min (5 min)
Column temperature: 40° C.
Sample temperature: 20° C.

TABLE 1

Typical retention times for acrylamide using the LC-MS/MS method described

| Compound | Retention time (min) |
|---|---|
| Acrylamide | 1.16 |
| $^{13}C_3$ Acrylamide | 1.16 |

MS Conditions
Ions were selected in order to achieve maximum sensitivity using multiple reaction monitoring.
Instrument: Waters Quattro Premier
Ionization mode: ES+
Desolvation temp.: 450° C.
Source temp.: 120° C.

TABLE 2

Positive Ion Mode - MRM Parameters

| MRM transition | RT | Compound ID | Cone, V | CE, V |
|---|---|---|---|---|
| 71.9-55.2 | 1.00 | Acrylamide | 23 | 8 |
| 74.9-58.2 | 1.00 | Acrylamide $^{13}C_3$ | 24 | 9 |

Dwell = 0.2 sec, Inter-channel delay = 0.005 sec

Figure 1:
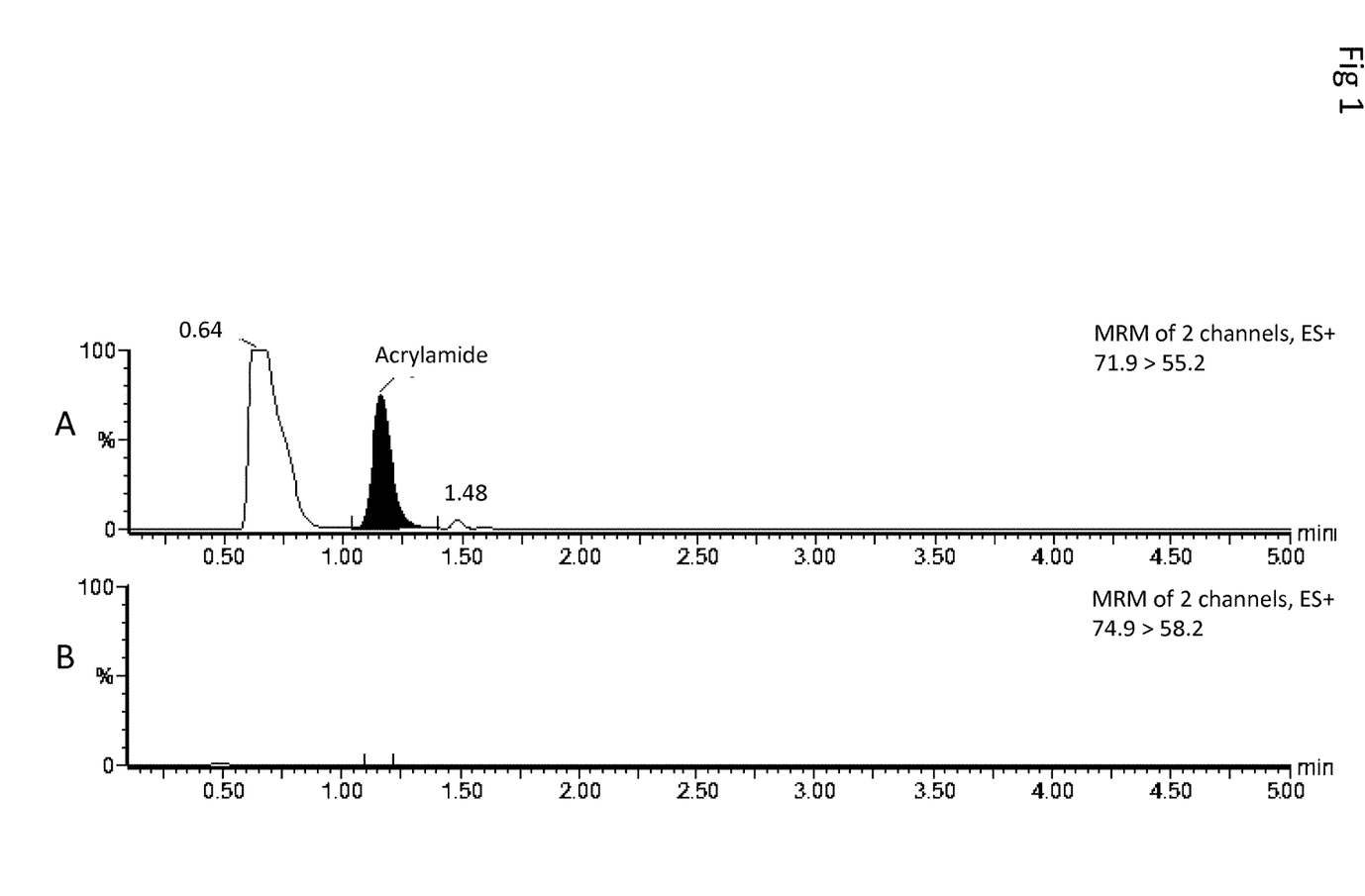
FIG. 1: Extracted ion chromatograms in positive ion mode using ISOLUTE SLE+ procedure (sample: 650 µL crisp extract, not spiked (process derived levels only). Top trace=Acrylamide, Bottom trace=$^{13}C_3$ Acrylamide on an equivalent scale.
Figure 2:
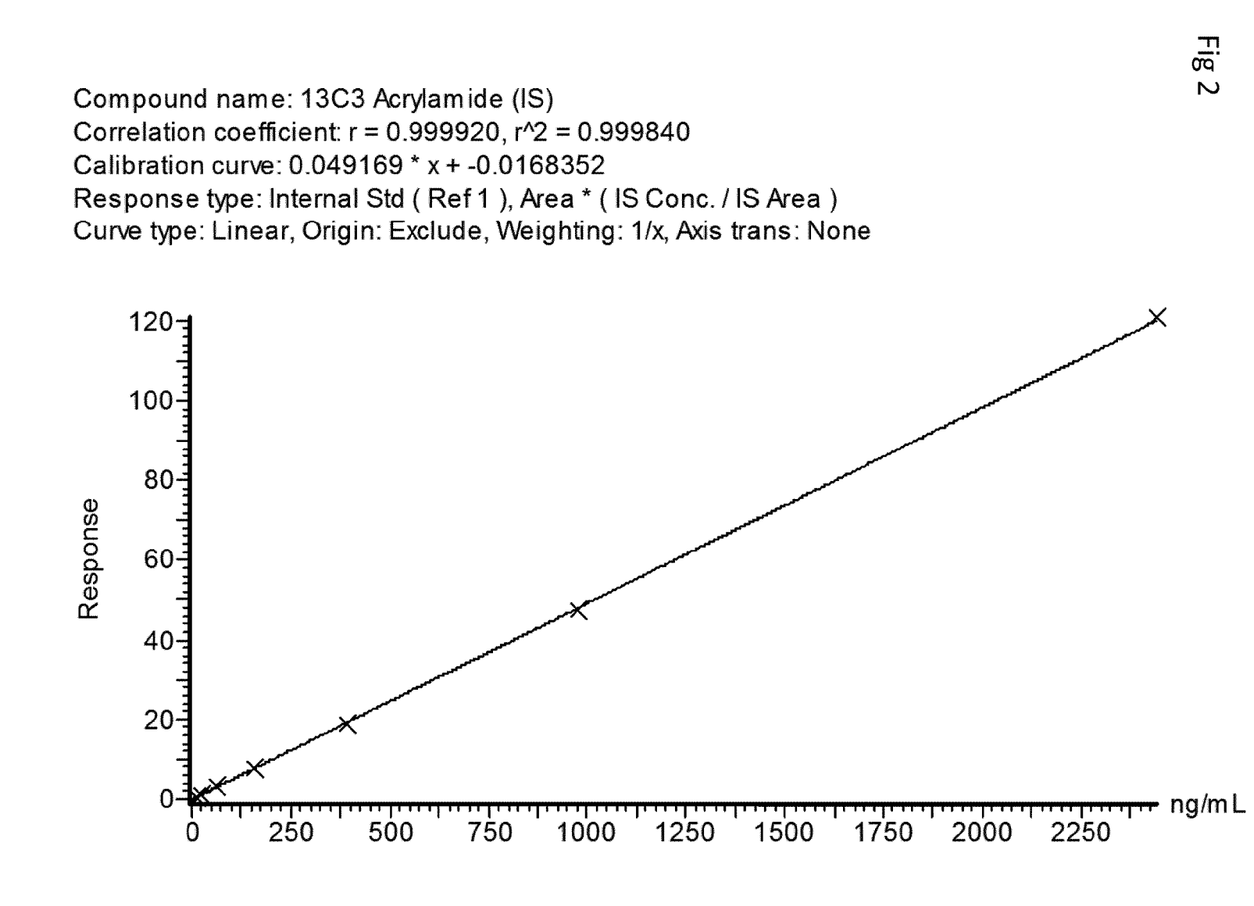
FIG. 2: Typical calibration curve for $^{13}C_3$ Acrylamide in ground potato crisps, expressed on a linear scale

Results
The results are shown in FIGS. 1 and 2.
FIG. 1 shows extracted ion chromatograms in positive ion mode using ISOLUTE SLE+ procedure (sample: 650 μL crisp extract, not spiked (process derived levels only). Top trace=Acrylamide, Bottom trace=$^{13}C_3$ Acrylamide on an equivalent scale.
FIG. 2. Typical calibration curve for $^{13}C_3$ Acrylamide in ground potato crisps/chips, expressed on a linear scale

TABLE 3

Performance and recovery data for acrylamide and internal standard

| Analyte | Recovery % | % RSD (n = 6) |
|---|---|---|
| Acrylamide | 90 | 6.3 |
| $^{13}C_3$ Acrylamide | 89 | 2.7 |

Recovery and RSD calculations based on extractions of blank matrix spiked at 1280 ng/mL without using an internal standard. The average blank response was subtracted from both extracted and fortified quantities prior to calculating both recovery and % RSD.

TABLE 4

Analyte performance from potato crisps/chips.

| Analyte | $r^2$ |
|---|---|
| Crisps | 0.9998 |

$r^2$ calculations were based on a 'reversed' calibration line. The analyte was the internal standard 13C3 acrylamide and the internal standard was acrylamide containing process derived and manually overspiked levels. Standards ranged from 10 to 1280 ng/g applying a weighting factor of 1/x.

Sensitive acrylamide calibration could not be directly demonstrated in crisps due to the presence of large levels of process produced analyte within the matrix giving a substantial intercept to the calibration line and inferior precision at low levels as a result. To demonstrate that analysis of acrylamide and its tri $^{13}$C equivalent was sensitive and consistent the calibration line was prepared of the internal standard, $^{13}C_3$ acrylamide instead. Spiked acrylamide was added to the process produced acrylamide already present within the crisps and used as the internal standard.

A calibration line extracted without crisps gave greater recoveries however the ratio of acrylamide to $^{13}C_3$ acrylamide was broadly similar so this could be investigated as a possible calibration line for low level acrylamide analysis.

The method was shown to work in salted and flavored potato chips (crisps) and also those that were labeled as "hand fried".

Ethylene Glycol was added in a small quantity prior to the extraction step to avoid the evaporated sample drying completely. Without this additive being present the majority of the acrylamide would be lost at this stage.

A 100% aqueous mobile phase was required to give retention to the polar analyte. This required a column that was designed to work under these conditions and the method included a relatively long equilibrium time between samples.

Example 2: Extraction of Acrylamide from Coffee Using ISOLUTE SLE+ Prior to LC-MS/MS Analysis This example describes a Supported Liquid Extraction (SLE) protocol for the extraction of Acrylamide from coffee using ISOLUTE SLE+ plates with LC-MS/MS detection.

Introduction

The method described in this example achieves high recoveries of acrylamide in coffee. The method is sensitive enough to measure levels as low as 1 ng/mL in coffee (solution), 25 ppm in ground coffee (solid) or 125 ppm in instant coffee (solid, traditional or decaffeinated) and gives good selectivity from what is a challenging matrix.

Sample Preparation Procedure
Column Configuration:
ISOLUTE® SLE+ 1000 supported liquid extraction plate, (Biotage, Uppsala Sweden, part number 820-0140-C).
Sample Pre-Treatment:
Coffee was prepared in the same way that it would normally be consumed. In the case of ground coffee 60 g of ground coffee was percolated with 1500 mL of boiling water. For instant coffee 2 g of instant coffee powder was dissolved in 250 mL of boiling water. This resulted in solutions containing coffee 'solid' concentrations of 40 mg/mL for ground coffee and 8 mg/mL for instant coffee. Once prepared the coffee was left to reach room temperature.
Calibration Line Preparation
A 128 ng/mL acrylamide coffee solution was prepared by diluting 25.6 µL of a 10 µg/mL aqueous acrylamide solution to 2 mL with control coffee.

This was then serially diluted seven times by transferring 0.8 mL, diluting with 0.8 mL of control coffee, mixing and then transferring another 0.8 mL of this mixture until a solution with an over-spiked level of 1 ng/mL had been reached.

0.625 mL aliquots were transferred to wells containing 10 µL of a 4 µg/mL $^{13}C_3$ acrylamide solution in water and 12.75 µL of a saturated solution of ammonium hydroxide in water.
Supported Liquid Extraction
Sample Work-Up:
Samples (0.625 mL) were transferred to tubes containing 10 µL of a 4 µg/mL $^{13}C_3$ acrylamide solution in water and 12.75 µL of a saturated solution of ammonium hydroxide in water. The tube was briefly shaken and then 0.5 mL of the mixture transferred to a 1 mL SLE cartridge.

Sample Loading:
Load pre-treated sample (0.5 mL) onto each well. Apply a pulse of vacuum (VacMaster-10 or 20 Sample Processing Manifold, 121-1016 or 121-2016 or positive pressure Pressure+ Positive Pressure Manifold, PPM-48) to initiate flow. Allow the sample to absorb for 5 minutes.

Analyte Elution:
Elute with Ethyl acetate: Tetrahydrofuran, (1:1, v/v, 2×2.5 mL) and allow to flow under gravity into a tube already containing 2 µL ethylene glycol. Apply vacuum or positive pressure to elute any remaining extraction solvent.

Post Elution:
Dry the volatile constituents of the eluate in a stream of air or nitrogen using an SPE Dry (ambient, 20 to 40 L min$^{-1}$), SD-9600-DHS or SD2-9600-DHS or TurboVap LV, C103198 or C103199 (15 bar at ambient for 1 hr). Reconstitute in water (200 µL).

HPLC Conditions
Instrument: Waters Acquity
Column: Phenomenex Hydro, 4 µm 50×2 mm C18 column with a C18 guard cartridge and on-line filter
Mobile Phase: A: 0.1% formic acid in water B: 0.1% formic acid in methanol
Flow rate: 0.3 mL min$^{-1}$
Injection: 10 µL
Gradient: Initial 100% A, hold till 0.6 min
linear ramp to 100% B over 0.25 min (0.85 min), hold 1.65 min (2.5 min)
linear ramp to 100% A in 0.01 min (2.51 min), hold 2.49 min (5 min)
Column temperature: 40° C.
Sample temperature: 20° C.

TABLE 5

Typical retention times for acrylamide using the LC-MS/MS method described

| Compound | Retention time (min) |
| --- | --- |
| Acrylamide | 1.02 |
| Acrylamide $^{13}C_3$ | 1.02 |

MS Conditions
Ions were selected in order to achieve maximum sensitivity using multiple reaction monitoring.
Instrument: Waters Quattro Premier
Ionization mode: ES+
Desolvation temp.: 450° C.
Source temp.: 120° C.

TABLE 6

Positive Ion Mode - MRM Parameters

| MRM transition | RT | Compound ID | Cone, V | CE, V |
| --- | --- | --- | --- | --- |
| 71.9-55.2 | 1.00 | Acrylamide | 23 | 8 |
| 74.9-58.2 | 1.00 | Acrylamide $^{13}C_3$ | 24 | 9 |

Dwell = 0.2 sec, Inter-channel delay = 0.005 sec

Figure 3:
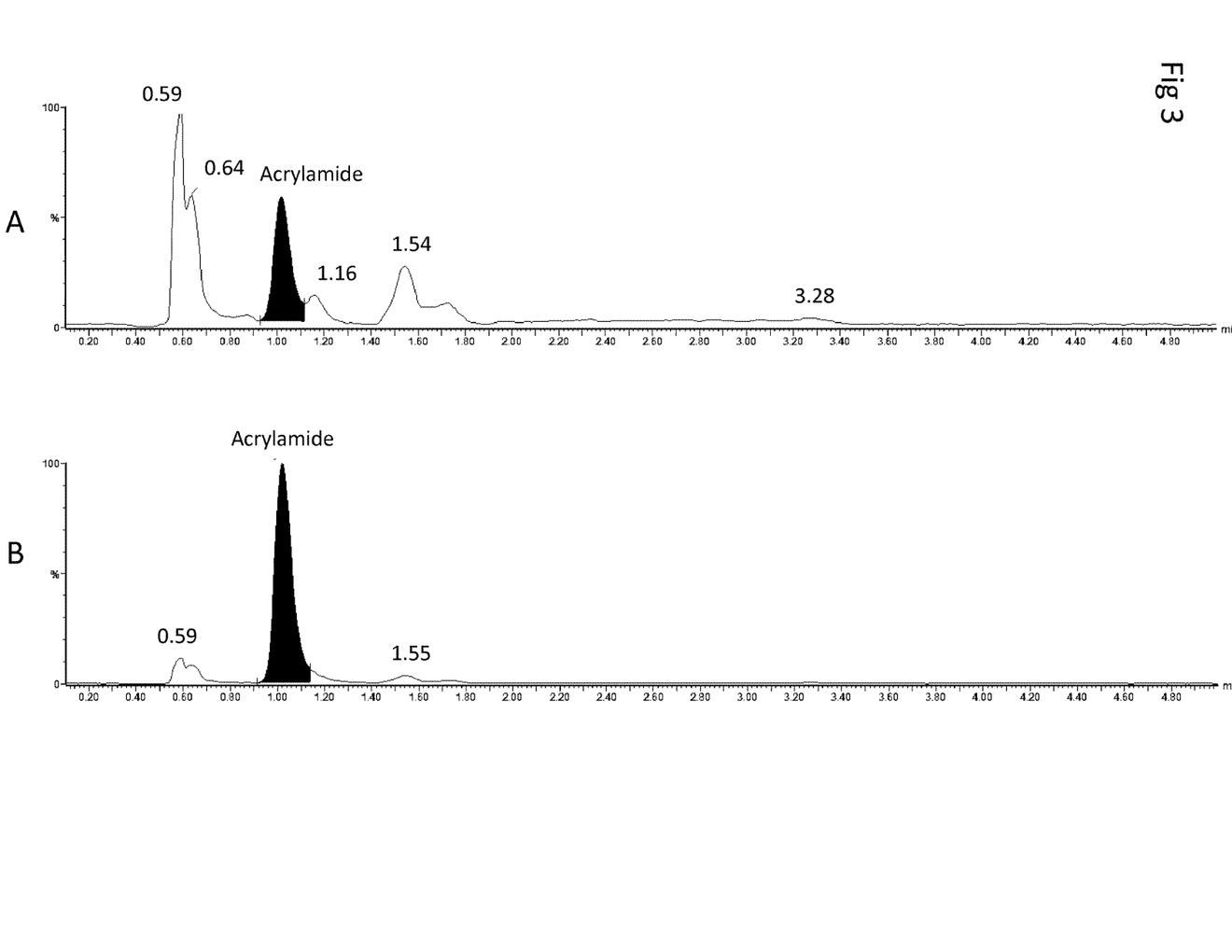
FIG. 3: Extracted ion chromatograms in positive ion mode using ISOLUTE SLE+ procedure (sample: 500 µL ground coffee, not spiked (process derived levels only) and over-spiked with 128 ng/mL acrylamide)
Figure 4:
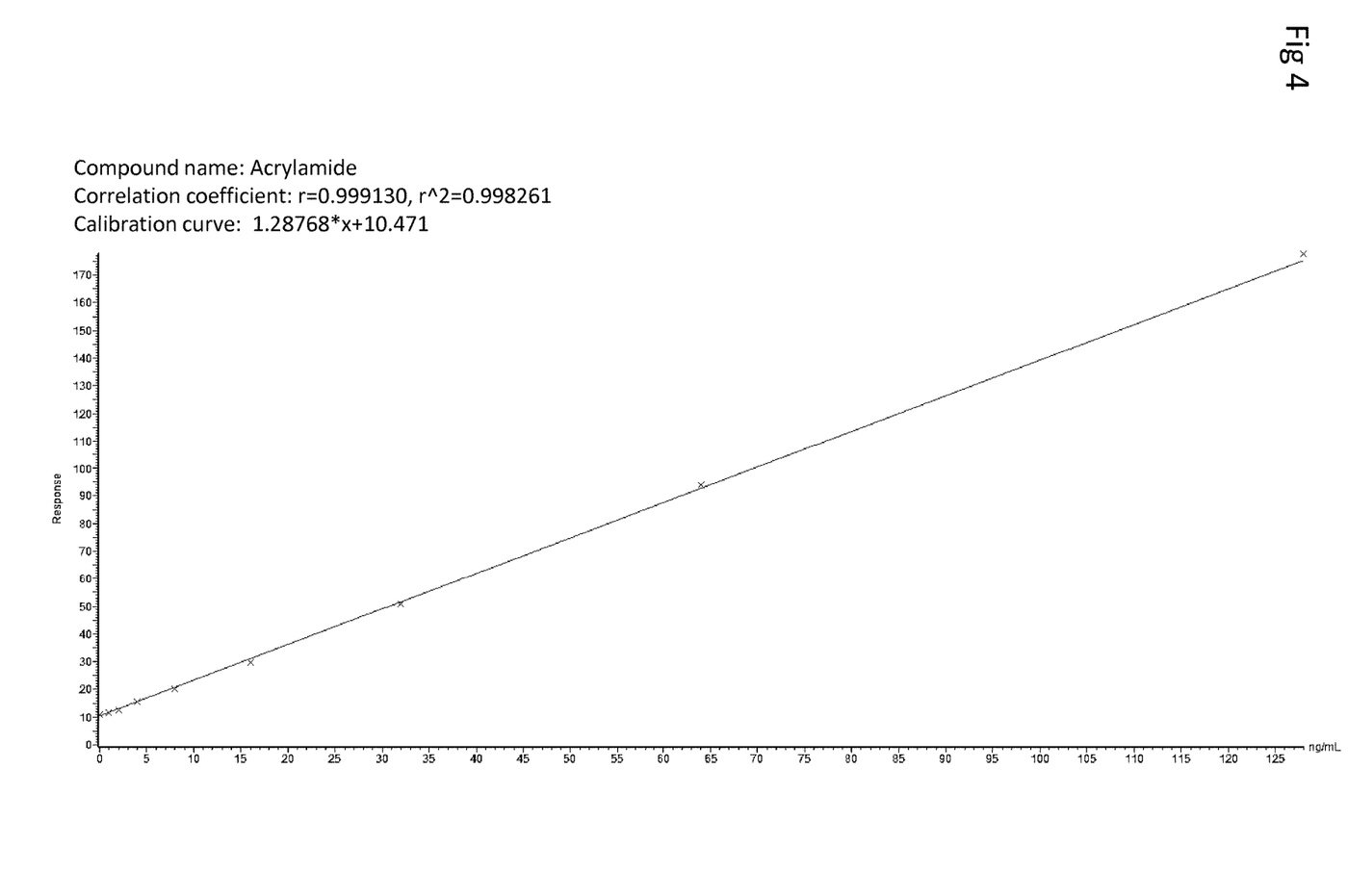
FIG. 4: Typical calibration curve for Acrylamide in ground coffee, expressed on a linear scale.

Results
The results are shown in FIGS. 3 and 4.
FIG. 3: Extracted ion chromatograms in positive ion mode using ISOLUTE SLE+ procedure (sample: (A) 500 µL ground coffee, not spiked (process derived levels only) and (B) over-spiked with 128 ng/mL acrylamide)

FIG. 4: Typical calibration curve for Acrylamide in ground coffee, expressed on a linear scale

TABLE 7

Performance and recovery data for acrylamide

| Acrylamide | Recovery % | % RSD (n = 6) |
|---|---|---|
| Fresh roast coffee | 81 | 8.2 |
| Instant coffee | 82 | 5.5 |
| Instant decaffeinated coffee | 73 | 3.7 |

Recovery and RSD calculations based on extractions of blank matrix spiked at 64 ng/mL without using an internal standard. The blank acrylamide response was subtracted from both extracted and fortified quantities prior to calculating both recovery and RSD.

TABLE 8

Analyte performance from ground coffee

| Analyte | $r^2$ |
|---|---|
| Ground coffee solution | 0.998 |

$r^2$ calculations were based on line including a 'zero' standard, over-spiked standards between 1 to 128 ng/mL and applying a weighting factor of 1/x.

The addition of the ammonia solution results in the coffee changing from a mid-brown to a darker brown appearance. Although the sample added to the SLE column is darker as a result of the basification the final extract appears visibly cleaner than with untreated coffee.

The majority of the coffee dyes are removed by being trapped on the SLE material.

Ethylene Glycol was added in a small quantity prior to the extraction step to avoid the evaporated sample drying completely. Without this additive being present the majority of the acrylamide would be lost at this stage.

A 100% aqueous mobile phase was required to give retention to the polar analyte. This required a column that was designed to work under these conditions and the method included a relatively long equilibrium time between samples.

Example 3

Comparison of Different SLE Environments

It was decided to test the extraction of acrylamide on a variety of SLE environments including different types of SLE from different manufacturers and in different quantities from both crisp extract and coffee.

SLE Types Investigated
Isolute SLE+ 400 (Biotage, Sweden)
Isolute HM-N 1 mL (Biotage, Sweden)
Thermo Hypersep 7 (Thermo Scientific)
Thermo Hypersep 9 (Thermo Scientific)
Method
Work-Up for Crisp Analysis:
1 g crisp samples (+/−0.01 g) were weighed into 15 mL centrifuge tubes
10 µL of internal standard was added to the tubes and allowed to dry for 30 minutes.
Add 10 mL water, rotate for 1 hour and centrifuge. The finished tubes had a thin oil layer above an aqueous extract layer above a solid (potato starch).

Work-Up for Coffee Analysis:
Remove 20 mL of coffee from the office coffee percolator
Allow to cool and then add 0.4 mL of concentrated ammonia solution
Mix and allow to stand for 5 minutes
Extraction
Add the aqueous crisp extract or coffee to the SLE bed. The volume of sample varied depending upon the size of SLE used. A volume of 0.5 mL was added to HM-N, 0.2 mL was added to the SLE+ and 0.1 mL was added to the Thermo plates as the capacity of these was not known.
Add ethyl:acetate:THF 1:1 to the SLE beds. The volume of solvent varied depending upon the SLE used. A volume of 5 mL was added to the HM-N, a total volume of 2 mL added to the others.
The ethyl acetate: THF was collected in an 8 mL glass tube containing 2 µL ethylene glycol for the HM-N or into a 2 mL collection block containing 2 µL ethylene glycol for the others.
Tubes originating from the HM-N extraction were dried down until only the ethylene glycol remained and combined with 200 µL water as a reconstitution solvent. These were then transferred to a separate block. Tubes originating from the other SLE varieties were already in a suitable block format so were simply combined with 200 µL reconstitution solvent.
Method Design
The following method was performed with each combination of matrix and SLE type as three different types of test.
Blank=Acrylamide levels measured were those inherently produced in the production of the coffee or crisps.
Extracted=As the blank except a significant quantity of acrylamide was added to the coffee or crisps during the sample work-up.
Fortified=As the blank except a quantity of acrylamide equivalent to a 100% extraction of the extracted tests was added to the final reconstitution solvent.
Multiple Blanks, fortified and extracted samples were run so that the precision could be assessed and any unusual results rejected.
Results

TABLE 9 extraction recoveries from different SLE - matrix types

| % recoveries | Ground coffee | Potato chip (crisp) extract |
|---|---|---|
| Isolute SLE+ | 70.4 | 75.9 |
| Isolute HM-N | 66.8 | 63.8 |
| Thermo Hypersep 7 | 53.9 | 53.0 |
| Thermo Hypersep 9 | 55.6 | 55.9 |

SLE+ and the two Thermo varieties gave good precision with a % RSD (% CV) of less than 3% for both crisp extract and coffee. The HM-N gave poorer precision data of between 14 and 15% for each. No results were rejected.
Calculations
For a simple method the extraction recovery would normally be calculated by the following equation:

$$\% \text{ recovery} = 100\% \times \frac{\text{average extract result}}{\text{average fortified result}}$$

However in the case of acrylamide there were levels present in all samples including the blanks A more accurate recovery calculation is the one below which was applied for all SLE-matrix combinations.

$$\% \text{ recovery (improved)} = 100\% \times \frac{\text{average extract result} - \text{average blank result}}{\text{average fortified result} - \text{average blank result}}$$

Conclusion

The results showed that all four types of SLE showed extraction of acrylamide. The results for SLE+ were better than the others which would be partly expected as the method performed was optimized more for this material.

The present invention is not limited to the above-described preferred embodiments. Various alternatives, modifications and equivalents may be used. Therefore, the above embodiments should not be taken as limiting the scope of the invention, which is defined by the appended claims.

Example 4: Use of Various Solvents

A range of water immiscible solvents were used for extraction of acrylamide from coffee. Extractions were performed essentially as described in Example 2, with the modification that 96 well SLE extraction plates (Biotage, Uppsala, Sweden) were used instead of SLE cartridges.

The content of acrylamide in the organic extract was analysed by LC-MS (Waters Alliance HT 2795 LC system connected to a Waters "Micromass Quattro Ultra Pt" triple quadrupole mass spectrometer). Recovery was calculated as peak response for the respective solvent as a percentage of the peak response for extraction with a 1:1 mixture of ethyl acetate:THF. The results are given in Table 10.

TABLE 10

| Extraction solvent | Acrylamide; peak response | Recovery |
|---|---|---|
| Ethyl Acetate | 2734 | 51% |
| Hexane | 5 | 0.1% |
| Heptane | 3 | 0.05% |
| Methyl Tert Butyl Ether | 677 | 12.6% |
| Dichloromethane (DCM) | 765 | 14.2% |
| DCM:IPA 95:5 | 1250 | 23.3% |
| Ethyl Acetate:Tetrahydrofuran 1:1 | 5370 | 100% |

Example 5: Use of Mixtures of Ethyl Acetate and Tetrahydrofuran (THF)

Preparation of Acrylamide Spiked Coffee Solution 5 mL of spiked coffee was prepared by spiking in acrylamide at a concentration of 50 ng/mL. 4.9 mL of this coffee was combined with 100 μL of a saturated solution of ammonium hydroxide, this was labelled "spiked". 4.9 mL of unspiked coffee was combined with 100 μL of a saturated solution of ammonium hydroxide, this was labelled "blank".

Preparation of Extraction Solvents

Six glass containers were taken these were then labelled and prepared as follows

TABLE 11

| Label | Ethyl Acetate added (mL) | THF added (mL) |
|---|---|---|
| "100% Ethyl Acetate" | 7 | 0 |
| "90% EA 10% THF" | 6.3 | 0.7 |
| "80% EA 20% THF" | 5.6 | 1.4 |
| "70% EA 30% THF" | 4.9 | 2.1 |
| "60% EA 40% THF" | 4.2 | 2.8 |
| "50% EA 50% THF" | 3.5 | 3.5 |

Preparation of Fortification Solution

A fortification solution was prepared by diluting acrylamide in acetonitrile at a concentration of 1 μg/mL Extraction Procedure 1. 0.18 mL of spiked matrix was added to 18 wells of an SLE 200 96 well block 2. 0.18 mL of blank matrix was added to 18 wells of the SLE 200 96 well block 3. A positive pressure pulse was applied to push the sample into the SLE material.

4. The SLE block was left for 5 minutes to equilibrate.

5. 1 mL of each of the extraction solvents were added to the wells, each solvent was added to three wells containing spiked matrix and three containing blank.

6. After 5 minutes a positive pressure was applied pushing any remaining solvent through and out of the material.

7. Solvents were collected into a 2 mL collection plate already containing 2 μL of ethylene glycol 8. Blank extracts were fortified by the addition of 9 μL of fortification solution (equivalent to 100% recovery)

9. Samples were evaporated* at room temperature

10. Evaporated* samples were reconstituted in 200 μL water

11. Results were normalised so that the average peak area of the fortified samples for each test gave a response of 100%, extracted samples were then measured against these

12.

* Ethylene glycol not evaporated

LC System Conditions

Column: Phenomenex Hydro, 4 μm 50×2 mm C18 column with a C18 guard cartridge and on-line filter Mobile Phase: A: 0.1% formic acid in water B: 0.1% formic acid in methanol Flow rate: 0.3 mL min−1

Injection: 10 μL

Gradient: Initial 100% A, hold till 0.6 min linear ramp to 100% B over 0.25 min (0.85 min), hold 1.65 min (2.5 min)

linear ramp to 100% A in 0.01 min (2.51 min), hold 2.49 min (5 min)

Column temperature: 40° C.

Sample temperature: 20° C.

MS-MS System Conditions

Ionization mode: ES+

Desolvation temp.: 450° C.

MRM & conditions Acrylamide 71.9 to 55.2, cone voltage=23, CE=8, 13C3 Acrylamide 74.9 to 58.2, cone voltage=24, CE=9

TABLE 12

Extraction recovery data

| | % Ethyl Acetate | | | | | |
|---|---|---|---|---|---|---|
| | 100 | 90 | 80 | 70 | 60 | 50 |
| % tetrahydrofuran | 0 | 10 | 20 | 30 | 40 | 50 |
| Fortified samples (normalised to an average response of 100%) | | | | | | |
| fortified 1 | 101.6 | 101.0 | 100.2 | 100.4 | 100.6 | 100.0 |
| fortified 2 | 100.2 | 98.8 | 101.0 | 99.3 | 100.1 | * |
| fortified 3 | 98.3 | 100.2 | 98.8 | 100.3 | 99.3 | * |
| Average | 100.0 | 100.0 | 100.0 | 100.0 | 100.0 | 100.0 |
| % RSD | 1.7 | 1.1 | 1.1 | 0.6 | 0.7 | |
| Extracted samples (on the same scale as the fortified samples for the same solvent) | | | | | | |
| spiked 1 | 46.1 | 52.1 | 61.4 | 67.2 | 76.8 | 82.5 |
| spiked 2 | 44.9 | 54.4 | 60.6 | 64.0 | 74.2 | 80.2 |
| spiked 3 | 45.1 | 54.7 | 61.1 | 67.7 | 70.1 | 85.1 |
| Average | 45.4 | 53.7 | 61.0 | 66.3 | 73.7 | 82.6 |
| % RSD | 1.3 | 2.7 | 0.7 | 3.0 | 4.6 | 3.0 |

REFERENCES

Biotage, 2013. *Isolute® SLE+ User Guide*, Uppsala, Sweden: Biotage.

Claus, A. a., 2005. A method for the determination of acrylamide in bakery products using ion trap LC-ESI-MS/MS. *Molecular Nutrition and Food Research*, 49(10), pp. 918-925.

Delatour, T. et al., 2004. Improved sample preparation to determine acrylamide in difficult matrixes such as chocolate powder, cocoa, and coffee by liquid chromatography tandem mass spectroscopy. *Journal of Agricultural and Food Chemistry*, Volume 52, pp. 4625-4631.

Friedman, M., 2003. Chemistry, Biochemistry, and Safety of Acrylamide. A Review. *Journal of Agricultural and Food Chemistry*, Volume 51, pp. 4504-4526.

Pule, B. & Torto, N., 2012. *Determination of acrylamide in cooking oil by Agilent Bond Elut QuEChERS Acrylamide kit and HPLC-DAD*, Grahamstown, South Africa: Agilent Technologies.

Roach, J. et al., 2003. Rugged LC-MS/MS Survey Analysis for Acrylamide in Foods. *Journal of Agricultural and Food Chemistry*, Volume 51, pp. 7547-7554.

Tareke, E. et al., 2002. Analysis of Acrylamide, a Carcinogen Formed in Heated Foodstuffs. *J. Agric. Food Chem.*, 50(17), pp. 4998-5006.

The invention claimed is:

1. A method for extracting acrylamide from a matrix, the matrix including matrix components and acrylamide, the method comprising:
    bringing said matrix in contact with water to generate an aqueous extract;
    adding a base to the aqueous extract to form a basified aqueous extract;
    loading a portion of the basified aqueous extract onto an inert support, such that the inert support absorbs the portion of the basified aqueous extract, wherein the inert support is diatomaceous earth; and
    extracting acrylamide from the basified aqueous extract based on passing a water immiscible organic solvent mixture of a first organic solvent and a second organic solvent through the inert support to form an organic extract, wherein the water immiscible organic solvent mixture is a mixture of ethyl acetate and tetrahydrofuran.

2. The method according to claim 1, wherein the water immiscible solvent includes a solvent that includes at least one of,
    ethyl acetate,
    methyl-tertiary butyl ether (MTBE),
    dichloromethane,
    chloroform,
    butanol,
    butyl acetate,
    dichloroethane,
    dichloromethane,
    diethyl ether,
    benzene,
    xylene, and
    toluene.

3. The method according to claim 1, wherein the water immiscible organic solvent mixture includes a mixture of the first organic solvent and the second organic solvent in a ratio of between about 2:1 and about 1:2.

4. The method according to claim 1, wherein the first organic solvent includes a solvent that includes at least one of,
    ethyl acetate,
    methyl-tertiary butyl ether (MTBE),
    dichloromethane,
    chloroform,
    butanol,
    butyl acetate,
    dichloroethane,
    dichloromethane,
    diethyl ether,
    benzene,
    xylene,
    toluene,
    hexane, and
    heptane.

5. The method according to claim 1, wherein the second organic solvent includes at least one of,
    tetrahydrofuran,
    n-propanol,
    iso-propanol,
    dioxane,
    acetone,
    methanol,
    ethanol,
    acetonitrile,
    acetic acid,
    dimethylformamide, and
    dimethyl sulfoxide.

6. The method according to claim 1, wherein the matrix is a food matrix.

7. The method according to claim 6, wherein the food matrix includes one of coffee and a plurality of potatoes.

8. A method for analysing acrylamide content in a matrix, the matrix including matrix components and acrylamide, the method comprising:
    extracting acrylamide from the matrix according to the method of claim 1;
    determining an acrylamide content of the organic extract formed according to the method of claim 1.

* * * * *